(12) United States Patent
Sasaki

(10) Patent No.: US 12,213,821 B2
(45) Date of Patent: Feb. 4, 2025

(54) X-RAY CT APPARATUS, DETERMINATION METHOD, AND STORAGE MEDIUM

(71) Applicant: CANON MEDICAL SYSTEMS CORPORATION, Otawara (JP)

(72) Inventor: Yu Sasaki, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 192 days.

(21) Appl. No.: 18/166,515

(22) Filed: Feb. 9, 2023

(65) Prior Publication Data
US 2023/0255578 A1 Aug. 17, 2023

(30) Foreign Application Priority Data
Feb. 16, 2022 (JP) ................... 2022-022249

(51) Int. Cl.
*A61B 6/42* (2024.01)
*A61B 6/03* (2006.01)

(52) U.S. Cl.
CPC ............ *A61B 6/4241* (2013.01); *A61B 6/032* (2013.01)

(58) Field of Classification Search
CPC ........ A61B 6/4241; A61B 6/032; A61B 6/586
See application file for complete search history.

(56) References Cited

U.S. PATENT DOCUMENTS

| | | | |
|---|---|---|---|
| 2005/0084063 A1* | 4/2005 | Heismann | A61B 6/508 378/53 |
| 2012/0014504 A1* | 1/2012 | Jang | A61B 6/482 378/37 |
| 2013/0083901 A1 | 4/2013 | Grasruck | |
| 2014/0177810 A1* | 6/2014 | Gao | H05G 1/54 378/207 |
| 2018/0325479 A1* | 11/2018 | Flohr | A61K 9/0019 |
| 2019/0290227 A1* | 9/2019 | Krauss | A61B 6/4035 |
| 2020/0249179 A1* | 8/2020 | Yamakawa | G01T 1/36 |
| 2020/0326290 A1* | 10/2020 | Iniewski | G01N 23/20008 |
| 2021/0022695 A1* | 1/2021 | Iniewski | A61B 6/58 |
| 2022/0211338 A1* | 7/2022 | Kojima | A61B 6/4241 |
| 2023/0255578 A1* | 8/2023 | Sasaki | A61B 6/4241 378/5 |
| 2023/0400422 A1* | 12/2023 | Iniewski | G01N 23/083 |
| 2024/0127501 A1* | 4/2024 | Tsuyuki | G06T 11/005 |
| 2024/0130701 A1* | 4/2024 | Tanaka | A61B 6/4241 |

* cited by examiner

*Primary Examiner* — David P Porta
*Assistant Examiner* — Gisselle M Gutierrez
(74) *Attorney, Agent, or Firm* — Oblon, McClelland, Maier & Neustadt, L.L.P.

(57) ABSTRACT

An X-ray CT apparatus of an embodiment includes a processing circuitry. The processing circuitry detects X-rays radiated from an X-ray tube in units of photons. The processing circuitry stores first energy spectrum information acquired by detecting X-rays at a first timing. The processing circuitry acquires second energy spectrum information by detecting X-rays at a second timing after the first timing. The processing circuitry determines a state of the X-ray tube on the basis of the first energy spectrum information and the second energy spectrum information.

7 Claims, 6 Drawing Sheets

X-RAY CT APPARATUS, DETERMINATION METHOD, AND STORAGE MEDIUM

CROSS-REFERENCE TO RELATED APPLICATION

The present application claims priority based on Japanese Patent Application No. 2022-022249 filed Feb. 16, 2022, the content of which is incorporated herein by reference.

BACKGROUND OF THE INVENTION

Field of the Invention

Embodiments of the present invention relate to an X-ray CT apparatus, a determination method, and a storage medium.

Description of Related Art

Conventionally, a photon counting type X-ray computed tomography apparatus (hereinafter referred to as a PCCT apparatus) using X-rays generated by an X-ray tube is known. The PCCT apparatus reconstructs a cross-sectional image of a subject by calculating the ratio of the count number of X-ray photons that have passed through the subject to the spectrum of the X-ray photons before passing through the subject (hereinafter referred to as an air radiation spectrum) in each of a plurality of energy bins or calculating a linear attenuation coefficient in each of a plurality of energy bins (energy bands).

An X-ray CT apparatus may be equipped with an X-ray tube with a design different from that recommended (hereinafter referred to as a non-genuine tube). The non-genuine tube differs in a target material and a target angle in the X-ray tube, a filter material and thickness, and the like, and thus has a different air radiation spectrum. In order to avoid mounting a non-genuine tube, there is a method of incorporating an electronic board in which an individual ID number is recorded in the X-ray tube and collating the ID number with a system. However, the collation method described above has problems such as restrictions on the design of a gantry due to changes in the external shape of the X-ray tube and an increase in weight, an increase in manufacturing costs, and the like.

Further, the material of the anode in the X-ray tube (hereinafter referred to as anode material) deteriorates according to long-term use of the X-ray tube in the X-ray CT apparatus. Deterioration of the anode material attenuates the output of soft X-rays (X-rays with low energy and low penetrability) in the air radiation spectrum. If the air radiation spectrum is different, the linear attenuation coefficient cannot be derived correctly, which may cause artifacts such as CT value shift in a reconstructed cross-sectional image. Therefore, in order to avoid CT value shift, it is necessary to know a net air radiation spectrum at the time of CT scanning. As described above, there are conventional cases in which the state of the X-ray tube cannot be determined efficiently.

DETAILED DESCRIPTION OF THE INVENTION

Figure 1:
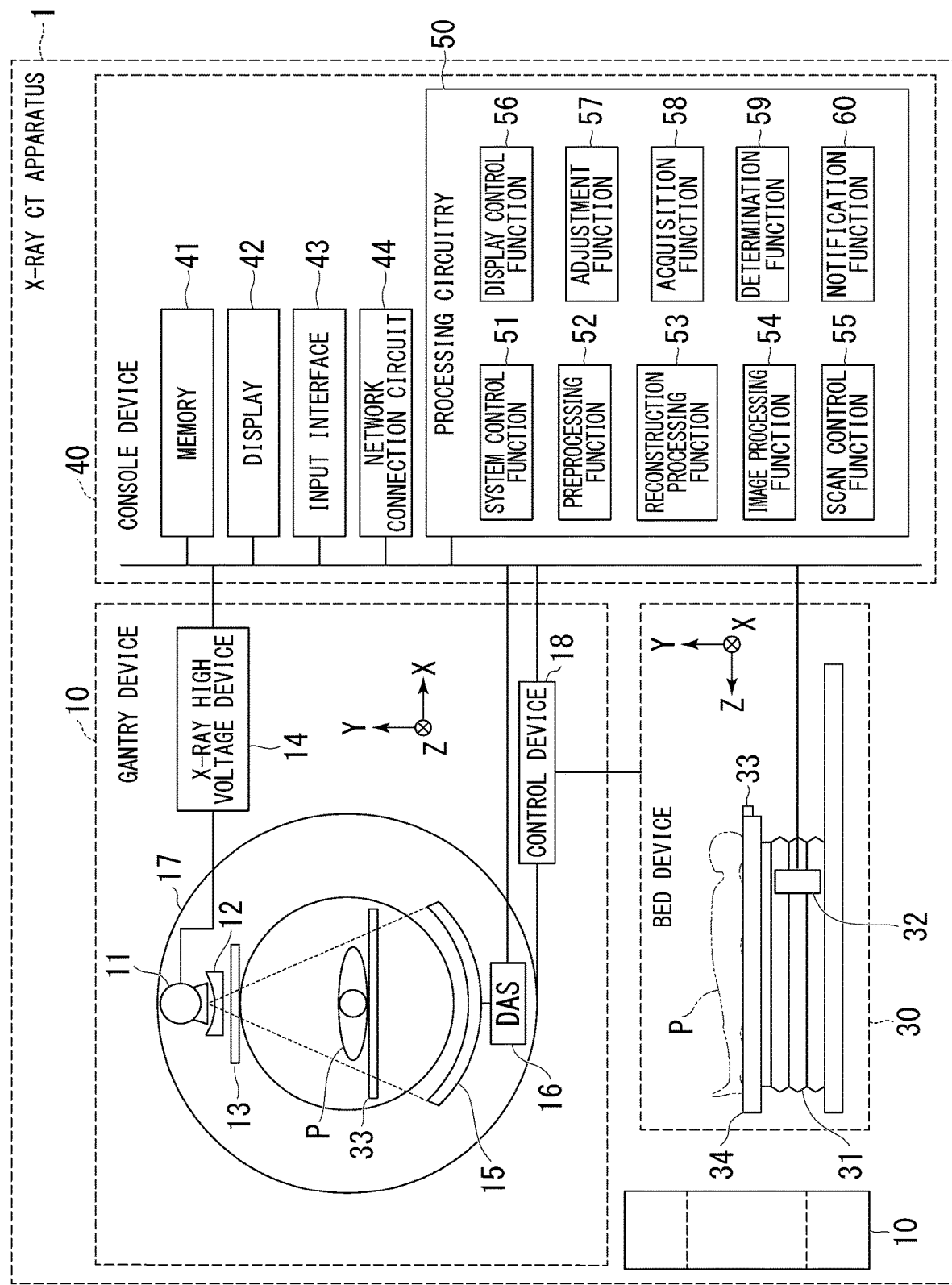
FIG. 1 is a configuration diagram of an X-ray CT apparatus according to an embodiment.

An X-ray CT apparatus, a determination method, and a storage medium according to an embodiment will be described below with reference to the drawings.

The X-ray CT apparatus of the embodiment includes a processing circuitry. The processing circuitry detects X-rays radiated from an X-ray tube in units of photons. The processing circuitry stores first energy spectrum information acquired by detecting X-rays at a first timing. The processing circuitry acquires second energy spectrum information by detecting X-rays at a second timing after the first timing. The processing circuitry determines a state of the X-ray tube on the basis of the first energy spectrum information and the second energy spectrum information.

In the following embodiments, parts denoted by the same reference numerals are assumed to perform the same operations and redundant descriptions will be omitted as appropriate. For specific description, an X-ray computed tomography apparatus according to an embodiment is described as a photon counting type X-ray computed tomography apparatus capable of performing photon counting CT (hereinafter referred to as an X-ray computed tomography (CT) apparatus). The X-ray CT apparatus is an apparatus capable of reconstructing X-ray CT image data with a high SN ratio by counting X-rays that have passed through a subject using a photon counting type X-ray detector (hereinafter referred to as a photon counting X-ray detector). The X-ray computed tomography apparatus according to the embodiment may have an integration type (current mode measurement type) X-ray detector instead of the photon counting X-ray detector.

FIG. 1 is a configuration diagram of an X-ray CT apparatus 1 according to an embodiment. The X-ray CT apparatus 1 includes a gantry device 10, a bed device 30, and a console device 40, for example. Although FIG. 1 shows both a diagram of the gantry device 10 viewed in the Z-axis direction and a diagram of the gantry device 10 viewed in the X-axis direction for convenience of description, there is a single gantry device 10. In the present embodiment, a rotation axis of a rotating frame 17 in a non-tilt state or the longitudinal direction of a top plate 33 of the bed device 30 is defined as the Z-axis direction, an axis orthogonal to the Z-axis direction and parallel to a floor surface is defined as the X-axis direction, and a direction orthogonal to the Z-axis direction and perpendicular to the floor surface is defined as the Y-axis direction.

The gantry device 10 includes, for example, an X-ray tube 11, a wedge 12, a collimator 13, an X-ray high voltage device 14, an X-ray detector 15, a data acquisition system (DAS) 16, the rotating frame 17, and a control device 18.

The X-ray tube 11 generates X-rays by radiating thermal electrons from a cathode (filament) to an anode (target) according to a high voltage applied from the X-ray high voltage device 14. The X-ray tube 11 includes a vacuum tube. For example, the X-ray tube 11 includes a rotating anode type X-ray tube that generates X-rays by radiating thermal electrons to a rotating anode. The X-ray tube 11 has a unique energy spectrum depending on the material/thickness of an X-ray filter, the material/thickness of a target, and a target angle. In the X-ray CT apparatus 1, it is important to provide an energy spectrum assumed by the system. The energy spectrum changes the contrast of a scanned image, and particularly in a PCCT apparatus, a change in the energy spectrum greatly affects the material discrimination performance.

The wedge 12 is a filter for adjusting an X-ray dose radiated from the X-ray tube 11 to a subject P. The wedge 12 is a filter that transmits and attenuates X-rays radiated from the X-ray tube 11 such that a distribution of an X-ray dose radiated from the X-ray tube 11 to the subject P becomes a predetermined distribution. For example, the wedge 12 is also called a wedge filter or a bow-tie filter. The wedge 12 is, for example, made by processing aluminum to have a predetermined target angle and a predetermined thickness.

The collimator 13 is a mechanism for narrowing down a radiation range of X-rays that have passed through the wedge 12. The collimator 13 narrows down a radiation range of X-rays by combining a plurality of lead plates to form a slit, for example. The collimator 13 may also be called an X-ray diaphragm.

The X-ray high voltage device 14 includes, for example, a high voltage generator and an X-ray controller. The high voltage generator has electrical circuits that include a transformer, a rectifier, and the like. The high voltage generator generates a high voltage to be applied to the X-ray tube 11. The X-ray controller controls the output voltage of the high voltage generator depending on an X-ray dose to be generated by the X-ray tube 11. The high voltage generator may boost the voltage using the transformer described above or boost the voltage using an inverter. The X-ray high voltage device 14 may be provided in the rotating frame 17 or may be provided on the side of a fixed frame (not shown) of the gantry device 10. The fixed frame is a support frame that allows the rotating frame 17 to be rotatable. The X-ray controller controls the output voltage of the high voltage generator depending on the X-ray dose to be generated by the X-ray tube 11.

The X-ray detector 15 is, for example, a photon counting X-ray detector (PCD). The X-ray detector 15 counts photons of X-rays generated by the X-ray tube 11. For example, the X-ray detector 15 detects X-rays that have been radiated from the X-ray tube 11 and passed through the subject P in units of photons and outputs an electrical signal corresponding to the X-ray dose to the DAS 16. Specifically, the X-ray detector 15 is configured to record the energy of each incident X-ray photon. After amplifying the detected output signal, the X-ray detector 15 counts the number of incident X-ray photons for each window divided according to a signal level, and thus the energy range of X-rays is recorded by a counter and arranged in a bin. The X-ray detector 15 has, for example, a plurality of detector element arrays in which a plurality of detector elements are arranged in a channel direction along one circular arc having the focal point of the X-ray tube 11 as the center. The X-ray detector 15 has, for example, a structure in which a plurality of detector element arrays are arranged in a slice direction (column direction or row direction).

Specifically, the X-ray detector 15 is, for example, an indirect conversion type detector having a grid, a scintillator array, and an optical sensor array. The scintillator array has a plurality of scintillators. The scintillators have scintillator crystals that output light with an amount of photons corresponding to an incident X-ray dose. The grid has an X-ray shielding plate that is arranged on the surface of the X-ray incidence side of the scintillator array and has a function of absorbing scattered X-rays. The grid may also be called a collimator (one-dimensional collimator or two-dimensional collimator). The optical sensor array has a plurality of optical sensor groups. An optical sensor group has a plurality of optical sensors. The optical sensor has a function of amplifying light received from a scintillator and converting the amplified light into an electrical signal. The optical sensor is, for example, a photo multiplier (PMT), an avalanche photo-diode (APD), or a silicon photo multiplier (SiPM). The optical sensor receives light from a scintillator and outputs an electrical signal (pulses) corresponding to incident X-ray photons. An electrical signal output by each detection element is also called a detection signal. The pulse height value (voltage) of this electrical signal (pulses) has a correlation with the energy value of X-ray photons. The X-ray detector 15 may be a direct conversion type detector having a semiconductor element that converts incident X-rays into an electrical signal. Further, the X-ray detector 15 is an example of an X-ray detection unit.

The DAS 16 includes, for example, an amplifier, an integrator, and an A/D converter. The amplifier amplifies an electrical signal output from each X-ray detection element of the X-ray detector 15. The integrator integrates the amplified electrical signal over a view period (which will be described later). The A/D converter converts an electrical signal representing the integration result into a digital signal. The DAS 16 outputs detection data based on the digital signal to the console device 40. The detection data is a digital value of X-ray intensity identified by a channel number and a row number of the X-ray detection element which is a generation source, and a view number indicating a collected view. A view number is a number that changes according to rotation of the rotating frame 17 and is a number that increments according to rotation of the rotating frame 17, for example. Therefore, the view number is information indicating the rotation angle of the X-ray tube 11. A view period is a period that falls between a rotation angle corresponding to a certain view number and a rotation angle corresponding to the next view number. The DAS 16 may detect switching of a view by a timing signal input from the control device 18, by an internal timer, or by a signal obtained from a sensor that is not shown. When X-rays are continuously emitted from the X-ray tube 11 during full scanning, the DAS 16 collects detection data groups for the entire circumference (for 360 degrees). When X-rays are continuously emitted from the X-ray tube 11 during half scanning, the DAS 16 collects detection data for a half circumference (for 180 degrees). Further, the DAS 16 is an example of a data collection unit.

The rotating frame 17 is an annular member that supports the X-ray tube 11, the wedge 12, the collimator 13, and the X-ray detector 15 while facing them. The rotating frame 17 is rotatably supported by the fixed frame around the subject P introduced therein. The rotating frame 17 further supports the X-ray high voltage device 14 and the DAS 16. The rotating frame 17 is rotatably supported by a non-rotating part (for example, the fixed frame which is not shown in FIG. 1) of the gantry device 10. A rotating mechanism includes, for example, a motor that generates a rotational driving force and a bearing that transmits the rotational driving force to the rotating frame 17 to rotate the rotating frame 17. The motor is provided, for example, in the non-rotating part, the bearing is physically connected to the rotating frame 17 and the motor, and the rotating frame rotates according to the rotational force of the motor.

The rotating frame 17 and the non-rotating part are provided with a non-contact type or contact-type communication circuit, whereby communication between a unit supported by the rotating frame 17 and the non-rotating part or an external device of the gantry device 10 is performed. For example, when optical communication is adopted as a non-contact communication method, detection data generated by the DAS 16 is transmitted from a transmitter having a light emitting diode (LED) provided in the rotating frame 17 to a receiver having a photodiode provided in the non-rotating part of the gantry device 10 through optical communication and further forwarded by the transmitter from the non-rotating part to the console device 40. In addition to non-contact type data transmission such as a capacitive coupling type and a radio wave type as a communication method, a contact type data transmission method using a slip ring and an electrode brush may be adopted. The rotating frame 17 is not limited to an annular member and may be a member such as an arm as long as it can support and rotate the X-ray tube 11 and the like.

Although the X-ray CT apparatus 1 is, for example, a rotate/rotate-type X-ray CT apparatus (third generation CT) in which both the X-ray tube 11 and the X-ray detector 15 are supported by the rotating frame 17 and rotate around the subject P, it is not limited thereto and may be a stationary/rotate-type X-ray CT apparatus (fourth generation CT) in which a plurality of X-ray detection elements arranged in an annular form are fixed to a fixed frame and the X-ray tube 11 rotates around the subject P.

The control device 18 includes, for example, a processing circuitry having a processor such as a central processing unit (CPU), and a driving mechanism including a motor, an actuator, and the like. The control device 18 receives an input signal from an input interface 43 attached to the console device 40 or the gantry device 10 and controls the operations of the gantry device 10 and the bed device 30.

The control device 18 rotates the rotating frame 17, tilts the gantry device 10, and moves the top plate 33 of the bed device 30, for example. When tilting the gantry device 10, the control device 18 rotates the rotating frame 17 about an axis parallel to the Z-axis direction on the basis of an inclination angle (tilt angle e) input to the input interface 43. The control device 18 ascertains the rotation angle of the rotating frame 17 from the output of a sensor which is not shown, or the like. Further, the control device 18 provides the rotation angle of the rotating frame 17 to a processing circuitry 50 at any time. The control device 18 may be provided in the gantry device 10 or may be provided in the console device 40. Further, the control device 18 is an example of a control unit.

The bed device 30 is a device on which the subject P that is a scanning target is placed and which is moved and introduced into the rotating frame 17 of the gantry device 10. The bed device 30 includes, for example, a base 31, a bed driving device 32, the top plate 33, and a support frame 34. The base 31 includes a housing that supports the support frame 34 such that the support frame 34 is movable in the vertical direction (Y-axis direction). The bed driving device 32 includes a motor and an actuator. The bed driving device 32 moves the top plate 33 on which the subject P is placed in the longitudinal direction (Z-axis direction) of the top plate 33 along the support frame 34. The top plate 33 is a plate-like member on which the subject P is placed.

The bed driving device 32 may move not only the top plate 33 but also the support frame 34 in the longitudinal direction of the top plate 33. Contrary to the above, the gantry device 10 may be movable in the Z-axis direction, and the rotating frame 17 may be controlled to come around the subject P according to movement of the gantry device 10. Moreover, both the gantry device 10 and the top plate 33 may be configured to be movable. Further, the X-ray CT apparatus 1 may be an apparatus in which the subject P is scanned in a standing or sitting position. In this case, the X-ray CT apparatus 1 includes a subject supporting mechanism instead of the bed device 30, and the gantry device 10 rotates the rotating frame 17 about the axial direction perpendicular to the floor surface. The X-ray CT apparatus 1 may not have the bed device 30. For example, when the opening of the X-ray CT apparatus 1 has a substantially cylindrical shape extending in the vertical direction, the subject is imaged in a standing position, and thus the bed device 30 is not necessary.

The console device 40 includes, for example, a memory 41, a display 42, an input interface 43, a network connection circuitry 44, and the processing circuitry 50. Although the console device 40 is described as being separate from the gantry device 10 in the embodiment, the gantry device 10 may include some or all of the components of the console device 40.

The memory 41 is realized by, for example, a random access memory (RAM), a semiconductor memory device such as a flash memory, a hard disk, an optical disk, or the like. The memory 41 stores, for example, projection data, reconstructed image (CT image) data, and the like. Such data may be stored in an external memory with which the X-ray CT apparatus 1 can communicate, instead of the memory 41 (or in addition to the memory 41). The external memory is controlled by the cloud server, for example, when the cloud server that manages the external memory receives a read/write request. The external memory is realized, for example, by a system called picture archiving and communication systems (PACS). The PACS is a system that systematically stores images and the like captured by various image diagnostic apparatuses. The memory 41 is an example of a storage unit.

Figure 2:
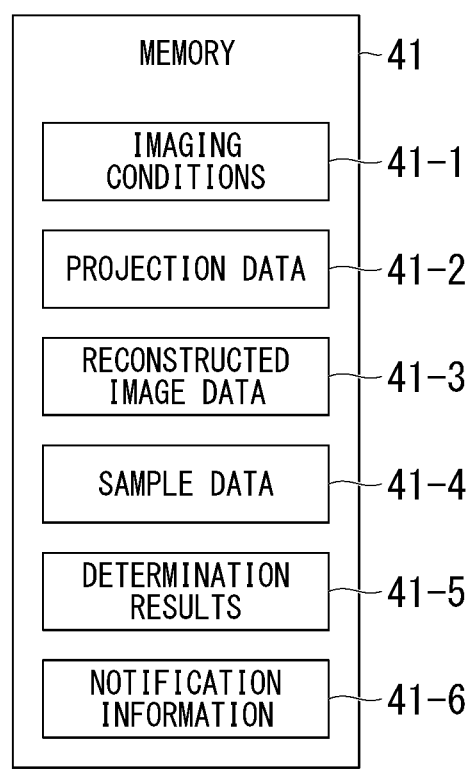
FIG. 2 is a diagram showing an example of data stored in a memory.

FIG. 2 is a diagram showing an example of data stored in the memory 41. As shown in FIG. 2, the memory 41 stores information such as imaging conditions 41-1 in which various conditions (scanning conditions and the like) at the time of imaging the subject P are set, projection data 41-2 generated by the processing circuitry 50, reconstructed image data 41-3, sample data 41-4 used to determine a difference in X-ray tube settings and a degree of deterioration, determination results 41-5, notification information 41-6, for example. The sample data 41-4 is first energy spectrum (radiation spectrum) information obtained by detecting X-rays from a genuine X-ray tube (genuine tube) which is a design recommended at a first timing. The first timing is, for example, the timing when the X-ray CT apparatus 1 is shipped. The timing of shipment may be a timing of shipment from a manufacturer to a sales destination, a timing at which initial setting (initial adjustment) is performed after installation at the sales destination, or the like. The notification information 41-6 is information in which notification content is associated with each state of the X-ray tube determined by a determination function 59. Further, the notification information 41-6 may include information on a notification destination (target).

The display 42 displays various types of information. For example, the display 42 outputs a medical image (CT image) generated by the processing circuitry 50, a graphical user interface (GUI) for receiving various operations by an operator, and the like. The display 42 is, for example, a liquid crystal display, a cathode ray tube (CRT) display, an organic electroluminescence (EL) display, or the like. The display 42 may be provided on the gantry device 10. The display 42 may be of a desktop type or may be a display device (for example, a tablet terminal) capable of wireless communication with the main body of the console device 40. Further, the display 42 is an example of a display unit.

The input interface 43 receives various input operations by the operator and outputs an electrical signal representing the content of a received input operation to the processing circuitry 50. For example, the input interface 43 receives input operations such as collection conditions at the time of collecting detection data or projection data, reconstruction conditions at the time of reconstructing a CT image, and image processing conditions at the time of generating a post-processed image from a CT image. For example, the input interface 43 is realized by a mouse, a keyboard, a touch panel, a trackball, a switch, a button, a joystick, a camera, an infrared sensor, a microphone, and the like. The input interface 43 may be provided in the gantry device 10. Further, the input interface 43 may be realized by a display device (for example, a tablet terminal) capable of wireless communication with the main body of the console device 40.

The network connection circuitry 44 includes, for example, a network card having a printed circuit board, a wireless communication module, or the like. The network connection circuitry 44 implements an information communication protocol in accordance with the form of a network that is a connection target. Networks include, for example, a local area network (LAN), a wide area network (WAN), the Internet, a cellular network, a dedicated line, and the like.

The processing circuitry 50 controls the overall operation of the X-ray CT apparatus 1. The processing circuitry 50 includes, for example, a system control function 51, a preprocessing function 52, a reconstruction processing function 53, an image processing function 54, a scan control function 55, a display control function 56, an adjustment function 57, an acquisition function 58, a determination function 59, a notification function 60 and the like. The processing circuitry 50 realizes these functions by a hardware processor executing a program stored in the memory 41, for example.

The hardware processor refers to, for example, a circuitry such as a CPU, a graphics processing unit (GPU), an application specific integrated circuit (ASIC), a programmable logic device (e.g., a simple programmable logic device (SPLD), a complex programmable logic device (CPLD), or a field programmable gate array (FPGA)). Instead of storing the program in the memory 41, the program may be directly embedded in the circuitry of the hardware processor. In this case, the hardware processor realizes the functions by reading and executing the program embedded in the circuitry. The hardware processor is not limited to being configured as a single circuit and may be configured as one hardware processor by combining a plurality of independent circuits to realize each function. Further, a plurality of components may be integrated into one hardware processor to realize each function. In addition, the processing circuitry 50 is an example of a processing unit. The acquisition function 58 is an example of an acquisition unit. The determination function 59 is an example of a determination unit. The notification function 60 is an example of a notification unit.

Each component of the console device 40 or the processing circuitry 50 may be distributed and realized by a plurality of pieces of hardware. The processing circuitry 50 may be realized by a processing device that can communicate with the console device 40 instead of being a component included in the console device 40. The processing device is, for example, a workstation connected to one X-ray CT apparatus, or a device (e.g., a cloud server) connected to a plurality of X-ray CT apparatuses and collectively executing processing equivalent to that of the processing circuitry 50 which will be described below. That is, the configuration of the present embodiment can also be realized as an X-ray CT system (medical diagnostic system) in which an X-ray CT apparatus and other processing devices are connected via a network.

The system control function 51 controls various functions of the processing circuitry 50 on the basis of input operations received through the input interface 43, for example.

The preprocessing function 52 performs preprocessing such as logarithmic conversion processing, offset correction processing, inter-channel sensitivity correction processing, and beam hardening correction on detection data output from the DAS 16 to generate projection data 41-2 and causes the memory 41 to store the generated projection data 41-2. Data before preprocessing (detection data) and data after preprocessing may be collectively referred to as projection data.

The reconstruction processing function 53 performs reconstruction processing on the projection data 41-2 generated by the preprocessing function 52 using a filtered back projection method, an iterative approximation reconstruction method, or the like to generate reconstructed image data (CT image data) 41-3 and causes the memory 41 to store the generated reconstructed image data 41-3.

The image processing function 54 converts the reconstructed image data 41-3 into three-dimensional image data or cross-sectional image data of an arbitrary cross-section by a known method on the basis of an input operation received through the input interface 43. Generation of three-dimensional image data may be performed by the reconstruction processing function 53.

The scan control function 55 controls detection data collection processing in the gantry device 10 by instructing the X-ray high voltage device 14, the DAS 16, the control device 18, and the bed driving device 32. The scan control function 55 controls the operation of each unit at the time of capturing an alignment image, an actual captured image, and an image used for diagnosis.

The display control function 56 controls a display mode of the display 42. For example, the display control function 56 controls the display 42 to display a reconstructed image generated by the processing circuitry 50, a GUI image for receiving various operations by the operator, and the like.

The adjustment function 57 controls adjustment processing when the X-ray CT apparatus 1 is shipped and when parts such as the X-ray tube 11 are exchanged. Adjustment processing includes, for example, calibration processing, IF adjustment (adjustment of a filament current value (IF value) of the X-ray tube 11) processing, seasoning (operation of preliminarily applying a load to the X-ray tube with a low voltage to increase the degree of vacuum inside the X-ray tube to remove residues, etc.) processing, and the like. The adjustment function 57 executes the above-described adjustment processing when an execution instruction from a user is received through the input interface 43, at a timing at which exchange of a target object (for example, an X-ray tube) is detected, a tube warm-up timing, or at a predetermined cycle.

The acquisition function 58 acquires data for determining design differences and a degree of deterioration of the X-ray tube 11 and the like. For example, the acquisition function 58 acquires the first energy spectrum information acquired by detecting X-rays at a timing (first timing) of adjusting operating conditions of equipment when the X-ray CT apparatus 1 is shipped and causes the memory 41 to store the acquired first energy spectrum information as sample data 41-4. Further, the acquisition function 58 may acquire the sample data 41-4 including the first energy spectrum information acquired from an external device via the network connection circuitry 44 and causes the memory 41 to store the first energy spectrum information.

In addition, the acquisition function 58 acquires second energy spectrum information acquired by detecting X-rays at a timing (for example, a second timing after the first timing) such as at the time of exchanging the X-ray tube 11. The acquisition function 58 may acquire the first energy spectrum information or the second energy spectrum information by being triggered by execution of predetermined adjustment processing (for example, IF adjustment) among the one or more types of adjustment processing executed by the adjustment function 57. In addition, the acquisition function 58 may execute processing of acquiring the first energy spectrum information or the second energy spectrum information when an execution instruction from the user is received through the input interface 43.

The determination function 59 determines the state of an object such as the X-ray tube 11 on the basis of the first energy spectrum information and the second energy spectrum information acquired by the acquisition function 58. Further, the determination function 59 causes the memory 41 to store the determination result as a determination result 41-5. Details of the determination function 59 will be described later.

The notification function 60 notifies a target of a notification content (warning and the like) according to the state of the X-ray tube determined by the determination function 59 among a plurality of notification contents included in notification information 41-6 stored in the memory 41. For example, the notification function 60 may display warning information on the display 42 and may notify a terminal (for example, a portable terminal such as a smartphone or a tablet terminal, or a fixed terminal) used by the target of the warning information via the network connection circuitry 44.

(Determination Function)

Next, the determination function 59 will be described in detail. The determination function 59 determines whether or not an object such as the X-ray tube 11 is a non-genuine product and determines a degree of deterioration of the object by determining the state of the object. In the following, the X-ray tube 11 is used as an example of the object. Further, in the following processing, it is assumed that the first energy spectrum information using a genuine product that is the X-ray tube 11 (genuine tube) has already been acquired at the first timing such as at the time of shipment and stored in the memory 41 as sample data 41-4.

Figure 3:
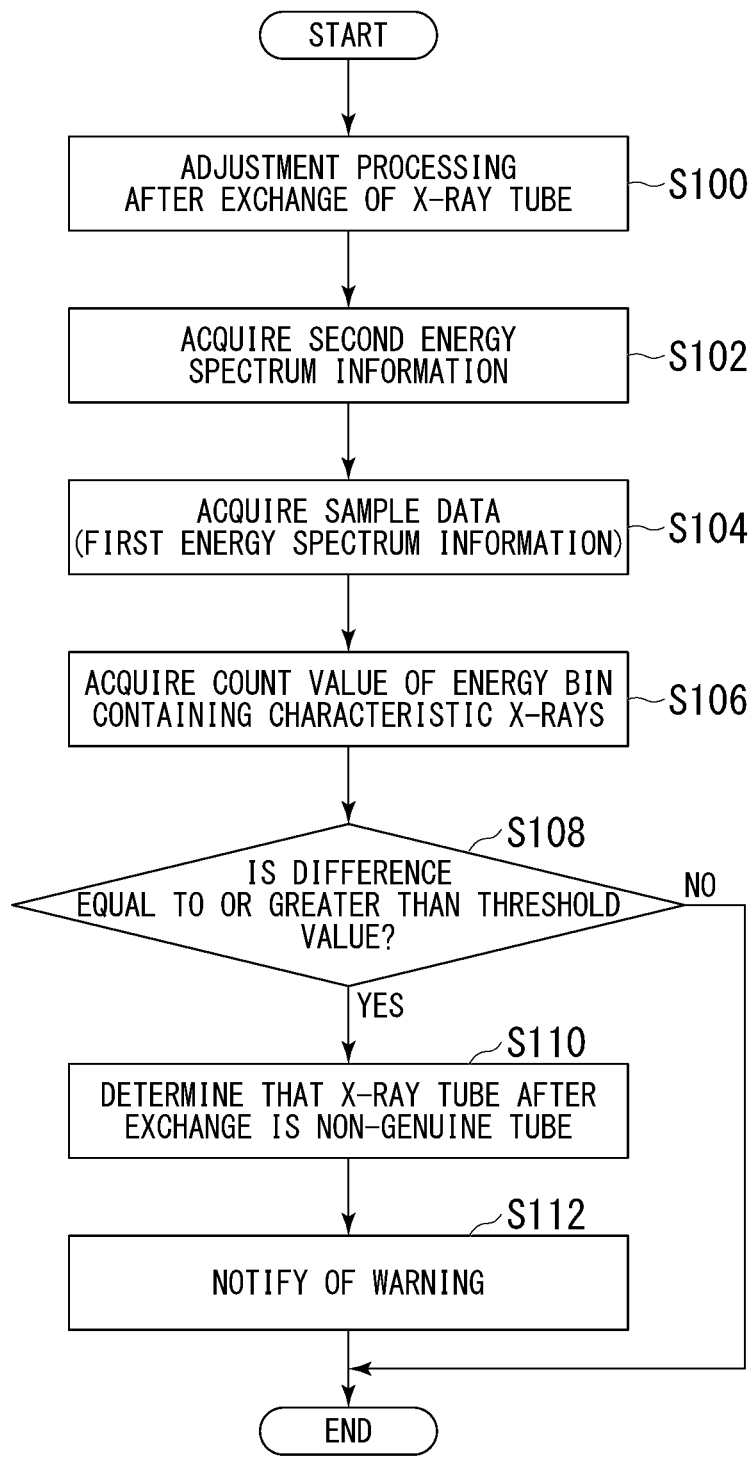
FIG. 3 is a flowchart showing an example of determination processing for determining whether or not an X-ray tube after exchange is a non-genuine tube.

FIG. 3 is a flowchart showing an example of determination processing for determining whether or not an X-ray tube 11 after exchange is a non-genuine tube. In the example of FIG. 3, after the X-ray tube 11 is exchanged, the adjustment function 57 executes adjustment processing of the X-ray CT apparatus 1 after exchange of the X-ray tube 11 (step S100). Next, the acquisition function 58 acquires the second energy spectrum information by being triggered by execution of predetermined processing in adjustment processing after exchange (step S102). Next, the acquisition function 58 acquires the first energy spectrum information which is the sample data 41-4 stored in the memory 41 (step S104). Next, the determination function 59 acquires a count value of an energy bin containing specific X-rays from each of the first energy spectrum information and the second energy spectrum information (step S106).

Figure 4:
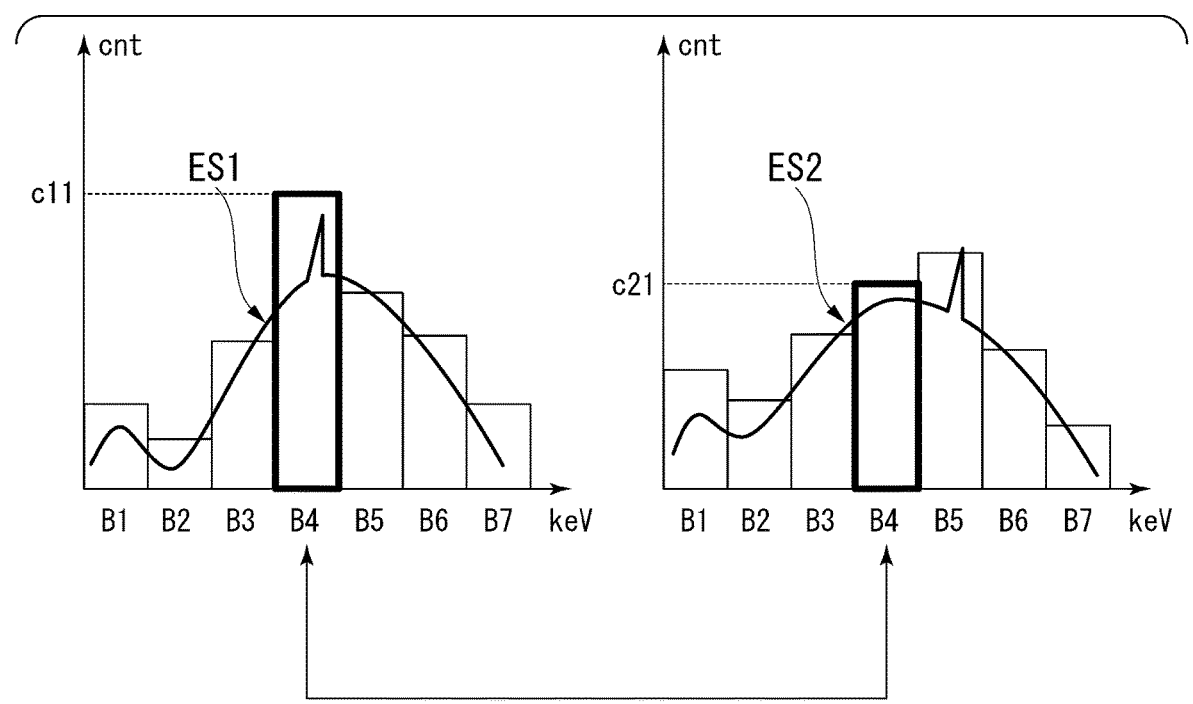
FIG. 4 is a diagram for describing comparison of count values of energy bins containing specific X-rays.

FIG. 4 is a diagram for describing comparison of count values of energy bins containing specific X-rays. In the example of FIG. 4, the horizontal axis represents energy (keV) and the vertical axis represents a count value (cnt) of photon counting. The example of FIG. 4 also shows the first energy spectrum ES1 obtained from the sample data 41-4 and the second energy spectrum ES2 acquired after exchange.

In the example of FIG. 4, energy bins (energy bands) B1 to B7 are set at predetermined intervals for each of the first energy spectrum ES1 and the second energy spectrum ES2. The energy bin intervals may be different intervals for each bin instead of the predetermined interval and may be arbitrarily set according to interval to be determined.

For example, the determination function 59 performs determination using a count value of an energy bin containing characteristic X-rays of the first energy spectrum ES1 obtained from the X-ray tube 11 which is a genuine tube among the energy bines shown in FIG. 4. Characteristic X-rays correspond to a portion in which a count value greatly varies depending on the material included in the X-ray tube 11, for example. The determination function 59 may perform comparison using a count value of an energy bin containing the energy of a K absorption edge regarding the anode material in the X-ray tube 11. In the example of FIG. 4, the determination function 59 acquires a count value (hereinafter referred to as a first count value) C11 of the energy bin B4 containing specific X-rays. Similarly, the determination function 59 acquires a count value (hereinafter referred to as a second count value) C12 of the energy bin B4 from the second energy spectrum ES2.

Referring back to FIG. 3, the determination function 59 determines whether or not the difference (difference value) between the first count value C11 and the second count value C12 is equal to or greater than a threshold value (step S108). When it is determined that the difference is equal to or greater than the threshold value, the determination function 59 determines that the X-ray tube after exchange is a non-genuine tube (step S110). Further, the determination function 59 may determine that the X-ray tube corresponding to the first energy spectrum information and the X-ray tube corresponding to the second energy spectrum information have different performances instead of determining that the X-ray tube after exchange is a non-genuine tube.

Next, the notification function 60 notifies a target of information (warning information) indicating that the exchanged X-ray tube is a non-genuine tube (step S112). Accordingly, processing of this flowchart ends. Further, in processing of step S108, if the difference between the first count value and the second count value is less than the threshold value, processing of this flowchart ends assuming that the X-ray tube after exchange is a genuine tube. In this case, the notification function 60 may notify the target of information indicating that the X-ray tube after exchange is a genuine tube.

As described above, the determination function 59 can determine the state of the X-ray tube more efficiently by narrowing down among all energy bins B1 to B7 to energy bins that change greatly due to the design of the X-ray tube 11 and performing determination. In determination processing described above, a difference in a target material may be determined on the basis of a determination result using energy bins containing characteristic X-rays with different energies emitted by the material of the X-ray tube target.

Further, in the above-described processing, when a count value of an energy bin differs due to differences in a filter material, thickness, and target angle, the energy bin may be used for determination. Moreover, the determination function 59 is not limited to a specific energy bin and may perform determination using all energy bins or may perform determination by comparing the first energy spectrum and the second energy spectrum.

Figure 5:
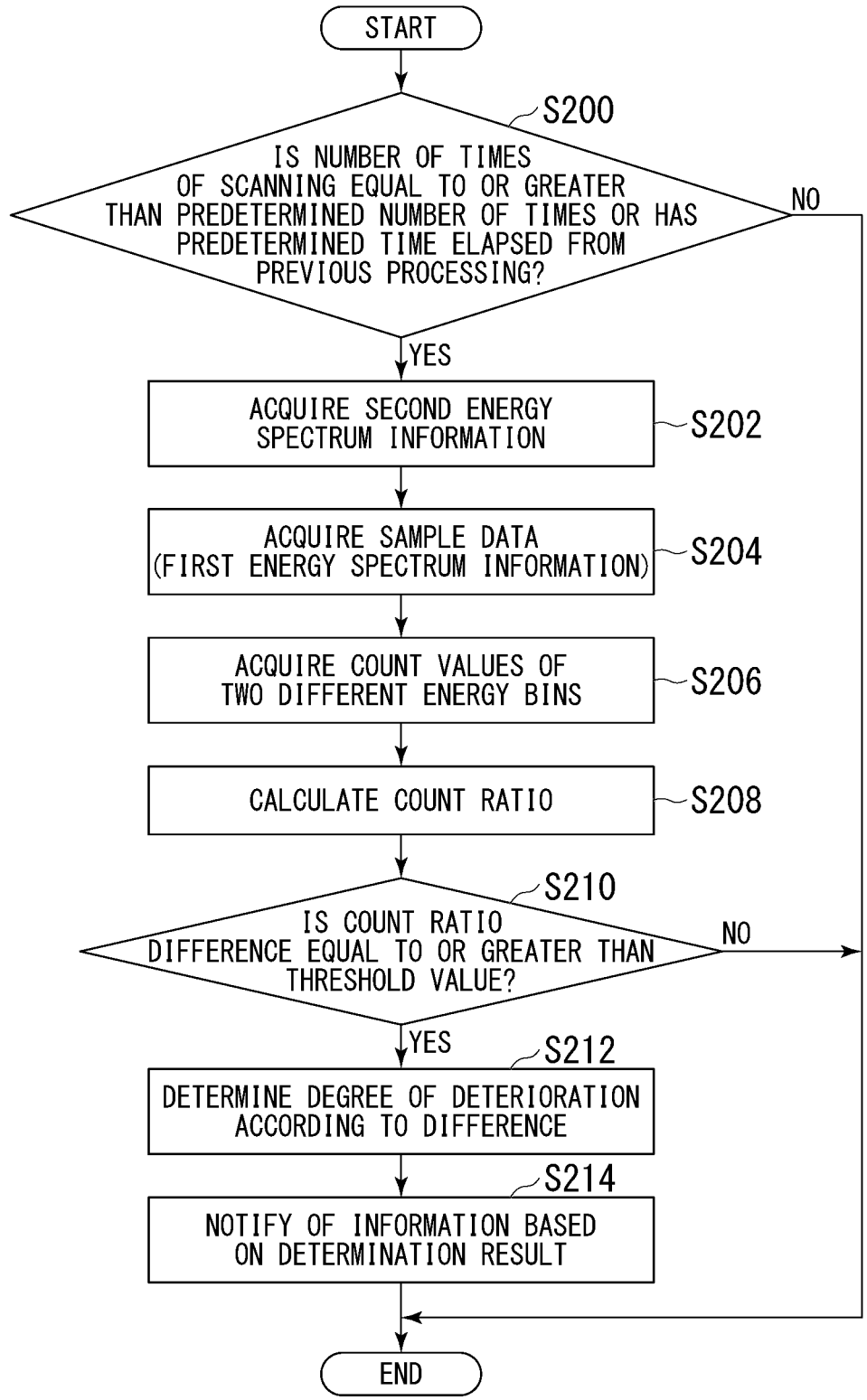
FIG. 5 is a flowchart showing a flow of a series of processing for determining a degree of deterioration.

Next, processing of determining a degree of deterioration of the X-ray tube in the determination function 59 will be described. FIG. 5 is a flowchart showing a flow of a series of processing for determining a degree of deterioration. It is assumed that the sample data 41-4 is stored in the memory 41 in advance in the example of FIG. 5.

In the example of FIG. 5, the determination function 59 determines whether or not the number of times of scanning (number of times of slicing) of the X-ray CT apparatus 1 is equal to or greater than a predetermined number of times or whether a predetermined time has elapsed from execution of the previous determination processing (step S200). If it is determined that the number of times of scanning is equal to or greater than the predetermined number of times or the predetermined time has elapsed from the previous processing, the acquisition function 58 acquires second energy spectrum information (step S202). Next, the acquisition function 58 acquires the sample data (first energy spectrum information) 41-4 from the memory 41 (step S204). Next, the determination function 59 acquires count values of two different energy bins from the acquired first energy spectrum information and second energy spectrum information (step S206).

Figure 6:
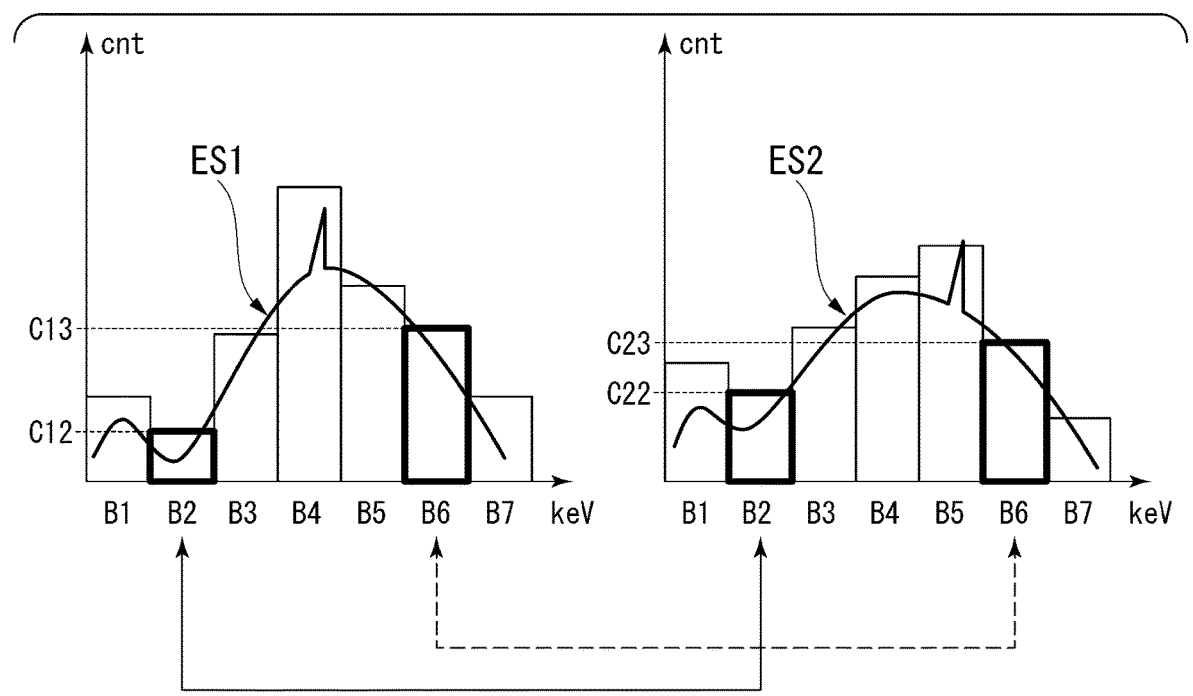
FIG. 6 is a diagram for describing acquisition of count values of two different energy bins.

FIG. 6 is a diagram for describing acquisition of count values of two different energy bins. In the example of FIG. 6, energy bins B1 to B7 are assigned to each of the first energy spectrum ES1 and the second energy spectrum ES2 as in FIG. 4. The determination function 59 obtains count values of two different energy bins from each of the first energy spectrum ES1 and the second energy spectrum ES2. In the two different energy bins, the energy bin with a lower energy is called the low energy bin and the energy bin with a higher energy is called the high energy bin.

In the example of FIG. 6, the determination function 59 acquires a count value C12 of the energy bin B2 and a count value C13 of the energy bin B6 of the first energy spectrum ES1. Similarly, the determination function also acquires a count value C22 of the energy bin B2 and a count value C23 of the energy bin B6 from the second energy spectrum ES2.

Referring back to FIG. 5, subsequently, the determination function 59 calculates the ratio of the count value of the low energy bin to the count value of the high energy bin in the first energy spectrum ES1 (for example, output ratio C12/C13) and the ratio of the count value of the low energy bin to the count value of the high energy bin in the second energy spectrum ES2 (for example, output ratio C22/C23) (step S208). Next, the determination function 59 determines whether or not the difference between the count ratios is equal to or greater than a threshold value (step S210). If it is determined that the difference is equal to or greater than the threshold value, the determination function 59 determines a degree of deterioration in accordance with the difference (step S212). In processing of step S212, the determination function 59 determines that the greater the difference, the greater the degree of deterioration, for example. Further, when the determination function 59 determines a degree of deterioration of the anode material, the determination function 59 may store a correspondence table of output ratios between low energy bins and high energy bins and anode thicknesses is stored in the memory 41 in advance and determine a degree of deterioration of the anode material with reference to the correspondence table. For example, the correspondence table is generated in advance through simulation, actual measurement, or the like before shipment of the X-ray CT apparatus 1. Further, the correspondence table may be stored in the sample data 41-4. Moreover, when a similar correspondence table is generated in advance for materials other than the anode material, the determination function 59 may determine a degree of deterioration for other materials in the same manner.

Next, the notification function 60 notifies the target of information based on the determination result (for example, information indicating a degree of deterioration or information indicating that maintenance is required) (step S214). Accordingly, processing of this flowchart ends. Further, if it is determined that the number of times of scanning is not equal to or greater than the predetermined number of times and that the predetermined time has not elapsed from the previous processing in processing of step S200, or it is determined that the difference between the count ratios is not equal to or greater than the threshold value in processing of step S210, processing of this flowchart ends.

In processing of step S200, processing after step S202 may be performed at any timing of the user (for example, at a timing indicated by a service person through the console). In determination processing described above, a degree of deterioration can be determined more efficiently and the target can be notified of a more accurate state.

Modified Examples

The above-described embodiment may be performed using a PCD as a reference (Ref) detector of a CT apparatus instead of using a main detector of a PCCT apparatus. Further, the sample data in the embodiment may be downloaded via a network or installed or updated by a recording medium such as a magnetic memory after shipment. In the embodiment, the determination function 59 may perform determination by changing (narrowing) the energy width of a bin such that an area including characteristic X-rays and an area including scattered X-rays are focused according to content to be determined.

According to at least one embodiment described above, the X-ray CT apparatus of the embodiment can determine the state of an X-ray tube more efficiently by including a photon counting X-ray detector that detects X-rays radiated from the X-ray tube in units of photons, a storage unit that stores first energy spectrum information acquired by detecting X-rays at a first timing, an acquisition unit that acquires second energy spectrum information by detecting X-rays at a second timing after the first timing, and a determination unit that determines the state of the X-ray tube on the basis of the first energy spectrum information and the second energy spectrum information.

Specifically, according to the present embodiment, an air radiation spectrum can be easily inspected, and an X-ray tube having an air radiation spectrum different from a recommended value can be detected, for example. Further, according to the embodiment, it is possible to detect an X-ray tube that provides an inappropriate air radiation spectrum that causes artifacts such as CT value shift and notify a target of the detected X-ray tube by comparing count of energy bins of energy spectrum sample data and the energy spectrum of the mounted X-ray tube. In addition, it is not necessary to introduce an external device that performs the conventional collation method in which an electronic board on which an individual ID number is recorded in an X-ray tube is built in and collation is performed in order to compare air radiation spectra using a PCD mounted in a PCCT apparatus, and it is possible to curb a change in the external shape of the apparatus, an increase in weight, and an increase in manufacturing costs.

The embodiment described above can be represented as follows.

An X-ray CT apparatus including:
a memory configured to store a program; and
a processor,
wherein the memory stores first energy spectrum information acquired by detecting X-rays at a first timing, and
by executing the program, the processor detects X-rays radiated from an X-ray tube in units of photons by a photon counting X-ray detector, acquires second energy spectrum information by detecting X-rays at a second timing after the first timing, and determines a state of the X-ray tube on the basis of the first energy spectrum information and the second energy spectrum information.

Although several embodiments have been described, these embodiments are presented as examples and are not intended to limit the scope of the invention. These embodiments can be implemented in various other forms, and various omissions, substitutions, and modifications can be made without departing from the spirit of the invention. These embodiments and modifications thereof are included in the scope and spirit of the invention, as well as the scope of the invention described in the claims and equivalents thereof.

What is claimed is:

1. An X-ray CT apparatus comprising a processing circuitry configured to:
   detect X-rays radiated from an X-ray tube in units of photons;
   store first energy spectrum information acquired by detecting X-rays at a first timing;
   acquire second energy spectrum information by detecting X-rays at a second timing after the first timing; and
   determine a state of the X-ray tube on the basis of the first energy spectrum information and the second energy spectrum information.

2. The X-ray CT apparatus according to claim 1, wherein the processing circuitry determines the state of the X-ray tube on the basis of a difference between a count value of photon counting in a predetermined energy bin included in the first energy spectrum information and a count value of photon counting in the predetermined energy bins included in the second energy spectrum information.

3. The X-ray CT apparatus according to claim 1, wherein the processing circuitry determines a degree of deterioration of the X-ray tube on the basis of a result of comparison between a count value of photon counting of each of two different energy bins among a plurality of energy bins included in the first energy spectrum information and a count value of photon counting of each of the two different energy bins among a plurality of energy bins included in the second energy spectrum information.

4. The X-ray CT apparatus according to claim 1, wherein the processing circuitry performs a predetermined notification for a target on the basis of the determined state of the X-ray tube.

5. The X-ray CT apparatus according to claim 1, wherein the first timing is a timing when a genuine X-ray tube is installed, the second timing is a timing when the X-ray tube is exchanged, and the processing circuitry determines whether or not the exchanged X-ray tube is a non-genuine X-ray tube.

6. A determination method, using a computer, comprising:
   detecting X-rays radiated from an X-ray tube in units of photons by a photon counting X-ray detector;
   storing first energy spectrum information acquired by detecting X-rays at a first timing in a storage unit;
   acquiring second energy spectrum information by detecting X-rays at a second timing after the first timing; and
   determining a state of the X-ray tube on the basis of the first energy spectrum information and the second energy spectrum information.

7. A non-transitory computer-readable recording medium storing a program of causing a computer to:
   detect X-rays radiated from an X-ray tube in units of photons by a photon counting X-ray detector;
   store first energy spectrum information acquired by detecting X-rays at a first timing in a storage unit;
   acquire second energy spectrum information by detecting X-rays at a second timing after the first timing; and
   determine a state of the X-ray tube on the basis of the first energy spectrum information and the second energy spectrum information.

* * * * *